United States Patent

Ersek et al.

Patent Number: 5,571,182
Date of Patent: *Nov. 5, 1996

[54] TEXTURED MICRO IMPLANTS

[76] Inventors: Robert A. Ersek, 62 Pascal, Austin, Tex. 78746; Arthur A. Beisang, III, 5883 Carlson St., Shoreview, Minn. 55126; Arthur A. Beisang, 1300 Ingerson Rd., Arden Hills, Minn. 55112

[*] Notice: The term of this patent shall not extend beyond the expiration date of Pat. No. 5,258,028.

[21] Appl. No.: 321,571

[22] Filed: Oct. 10, 1994

Related U.S. Application Data

[63] Continuation of Ser. No. 52,414, Apr. 22, 1993, abandoned, which is a continuation of Ser. No. 714,273, Jun. 12, 1991, Pat. No. 5,258,028, which is a continuation-in-part of Ser. No. 282,671, Dec. 12, 1988, abandoned.

[51] Int. Cl.⁶ .................................................. A61F 2/02
[52] U.S. Cl. ........................................ 623/11; 623/66
[58] Field of Search ............................ 623/11, 16, 66; 606/77, 92

[56] References Cited

U.S. PATENT DOCUMENTS

| | | | |
|---|---|---|---|
| 4,138,382 | 2/1979 | Polmanteer. | |
| 4,197,846 | 4/1980 | Bucalo | 128/218 P |
| 4,565,580 | 1/1986 | Miyata et al. | 106/124 |
| 4,678,470 | 7/1987 | Nashef et al. | 623/16 |
| 4,837,285 | 6/1989 | Berg et al. | 530/356 |
| 4,863,472 | 9/1989 | Tormal et al. | 623/16 |
| 5,067,965 | 11/1991 | Ersek et al.. | |
| 5,258,028 | 11/1993 | Ersek et al. | 623/11 |

FOREIGN PATENT DOCUMENTS

| | | |
|---|---|---|
| 0206726 | 12/1986 | European Pat. Off.. |
| 0251695 | 1/1988 | European Pat. Off.. |
| 2139898 | 11/1984 | United Kingdom. |
| 2227176 | 7/1990 | United Kingdom. |
| 8603671 | 7/1986 | WIPO. |
| 8807355 | 9/1987 | WIPO. |
| 8806873 | 9/1988 | WIPO. |
| 8805521 | 10/1988 | WIPO. |

OTHER PUBLICATIONS

Dupont, Production Bulletin "Nen–Trac Microspheres", pp. 1–8, 1988.

Primary Examiner—Debra S. Brittingham
Attorney, Agent, or Firm—Haugen and Nikolai, P.A.

[57] ABSTRACT

An improved micro-implantation method and composition for filling depressed scars, unsymmetrical orbital floors, muscle, lip, and other soft tissue defects is provided for use in reconstructive surgery procedures. Textured micro particles having an outside diameter between about 30 microns and 3000 microns are used with an appropriate physiologic vehicle cannula and syringe and/or pressure delivery system into a predetermined locus. The particles provide long-term filling of defects without migration loss.

20 Claims, 2 Drawing Sheets

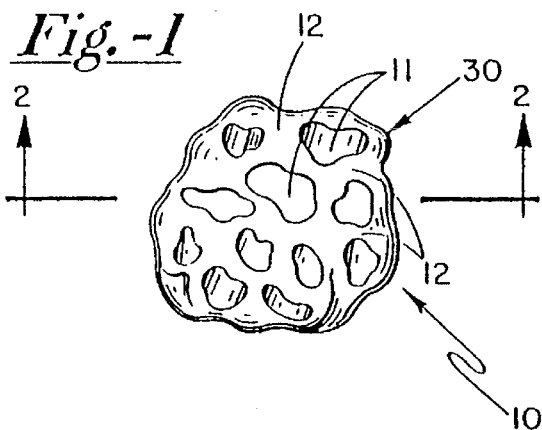
Fig.-1
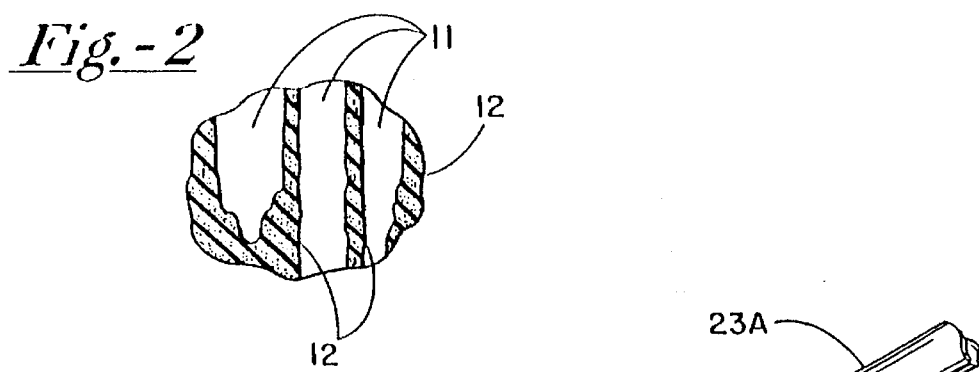
Fig.-2
Fig.-3
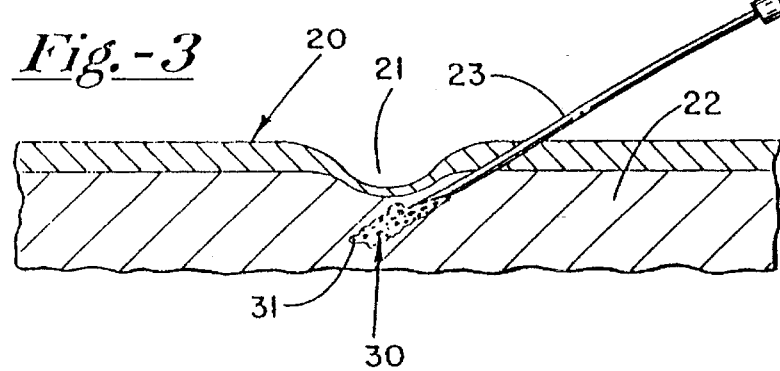
Fig.-4
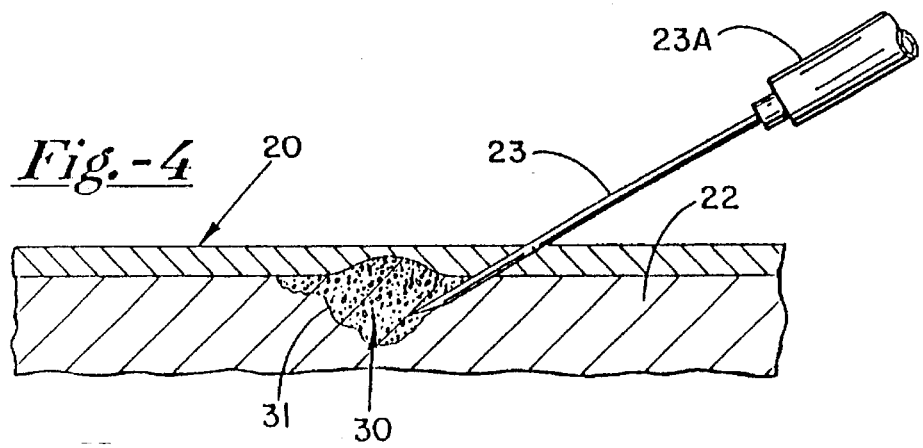

TEXTURED MICRO IMPLANTS

CROSS-REFERENCE TO RELATED APPLICATIONS

This is a continuation of application Ser. No. 08/052,414, filed Apr. 22, 1993, abandoned, which is, in turn, a continuing application of Ser. No. 07/714,273, filed Jun. 12, 1991, now U.S. Pat. 5,258,028 issued Nov. 2, 1993, which is a continuation-in-part of application Ser. No. 07/282,671, filed Dec. 12, 1988, now abandoned.

BACKGROUND OF THE INVENTION

The present invention relates generally to the field of surgery and more particularly to surgery directed to the repair of injuries or defects, usually considered plastic and reconstructive surgery of the human body.

In the practice of plastic and reconstructive surgery, it is often necessary to employ the use of tissue or foreign materials to provide a means to fill in defects which may be present in the human body. One such defect which occurs is enophthalmus wherein one eyeball cannot be coordinated with the other due to differences in the volume of the orbital contents which may have been created by either trauma or developmental anomaly. Such a volume defect prevents coordination of binocular vision, interferes with appropriate opening and closing of defective eyelids, and adversely affects appearance.

Another exemplary defect is an uneven vermillion border that is the result of a laceration, or from a cleft lip surgical repair. During the initial opposition of the separated tissues, there is tension and resultant loss of three dimensional symmetry of structure. By increasing the volume of the lip, three dimensional symmetry of structure is restored and the vermillion border is not disrupted. Paralysis or ablution of the vocal cords causing aphonia or dysphonia may be corrected by such augmentation. Traumatic or surgically altered bones, skin and subcutaneous tissue often have similar defects that interfere with form, function, or both.

In the practice of plastic and reconstructive surgery, inert materials have frequently been implanted to fill these defects. Recently, various collagen compounds and fibrin matrices have been injected to fill these defects. Bioactive materials such as hydroxyapatite or cordal granules (osteo conductive) have been used for hard tissue defects. Another prior art technique is to use adjacent or distant autologous tissues. Also, but on a rare or infrequent basis, cadaver and other species tissues have been used for fill-in substances. Liquid silicone has been used in the past as an injectable substance for very small defects. Although some scar tissue forms around the silicone liquid droplets, it is subject to rampant and distant migration throughout the body and the ultimate location for such substances tends to be unpredictable. As a result, liquid silicone has generally been viewed as a dangerous substance by most plastic surgeons. Although it has been useful in controlled studies in very small (one-tenth of a cc. to 1 cc.) injections, it is currently not approved for general use because of its tendency to migrate.

While it has been suggested to compound certain very small particle species in a lubricious material and to inject such combination micro particle media subcutaneously for both soft and hard tissue augmentation, heretofore success has been limited. Undesirable subsequent particle migration and serious granulomatous reactions commonly resulted. This is well documented with such materials as polytetrafluoroethylene spheres of very small diameter (>90% of a diameter ≦30 microns) in glycerine. See, for example, Malizia, et al., JAMA, Volume 251, No. 24, pp. 3277–3281 (1984), as a typical commentary or evaluation. The use of very small diameter particulate spheres (approximately 1–20 microns) or small diameter elongated fibrils, (generally 1–30 microns in diameter) of various materials such as cross-linked collagen in a biocompatible fluid lubricant as injectable implant compositions are disclosed in U.S. Pat. No. 4,803,075. While these materials create immediate augmentation, they also have a tendency to migrate and/or be reabsorbed from the injection site.

In accordance with the present invention, very small particles or micro particles and, in particular, textured micro particles are employed as an injectable solid substance for use in reconstructive surgical procedures. Textured micro particles having an outside diameter of between about 30 and 3000 microns (or between approximately 0.003 and 0.3 cm.) may be injected into the body along with an appropriate physiologic vehicle to enable the filling of defects. Accordingly, and in accordance with the present invention, textured micro particles to be described in more detail hereinafter may be employed which are fabricated from an elastomer such as silicone, an inert material such as polytetrafluoroethylene (Teflon), bioactive materials such as hydroxyapatite, ceramics or other inert substances. These textured micro particles may be introduced and placed at a precise location, and because of the textured configuration, tissue ingrowth will prevent dislodgement and ultimate migration. Furthermore, any over-correction can be readily adjusted by use of blunt cannulas and suction which provides for safe removal.

SUMMARY OF THE INVENTION

In accordance with the present invention, textured micro particles having a nominal diameter of between about 30 and 3000 microns (0.003 to 3.0 mm) are selected. These textured micro particles present generally amorphous surfaces, and normally possess indentations ranging in size from, for example, 10Å (angstroms) to 500 microns with the indentations having irregular configurations and surfaces. Furthermore, a minimal inter-indentation distance is provided so that the particles may be injected through an appropriate hypodermic needle of the appropriate preselected size, and with or without an appropriate physiologic vehicle. Examples of appropriate physiologic vehicles are saline, various starches, hydrogels, polyvinylpyrrolidones, other polymeric materials, polysaccharides, organic oils or fluids, all of which are well known and utilized in the art. Vehicles that are biologically compatible, i.e., cause minimal tissue reaction and are removed or metabolized without cytotoxicity, are, of course, utilized.

Biologically compatible saccharides such as glucose have been found useful. Vehicles such as aqueous solutions of starch may also be employed. In certain instances, it may be desirable to employ a totally inert vehicle such as silicone oil or the like. Certain fats may also be found useful. In this connection, highly compatible vehicles include esters of hyaluronic acids such as ethyl hyaluronate and polyvinylpyrrolidone (PVP). PVP normally has the general empirical formula $[(CHCH_2)_2N(CH_2)_3CO]_n$ wherein n equal 25–500, a form of which is otherwise known and marketed as Plasdone™ (trademark of GAF Corporation, New York, New York). Additionally, polyvinylpyrrolidone (Plasdones), hyaluronate, collagen and other biocompatible substances may be incorporated into the elastomer or combined with its surface. Another biocompatible vehicle is the patient's own plasma. Blood may be withdrawn from the patient, centrifuged to remove cells (or not) and mixed with appropriate aliquots of particles and the mixture injected in the desired locations.

It certain instances, it has been found desirable to utilize a surface modifier in combination with the micro particles, with materials such as polyvinylpyrrolidone, collagen, or hyaluronates having been found suitable. A surface modifier may be defined generally as a material combined into the formed particle, applied to the surface of the particle or added to the carrier vehicle to alter inter-particle or prosthesis-host interaction and/or particle identifiability. These surface modifiers may alter the coefficient of friction of the particles as by making them more lubricious, render the particles more radiopaque, assist in detoxification, and/or render the surface of the particles more susceptible to tissue ingrowth.

In this connection, the surface modifiers such as polyvinylpyrrolidone or polytetrafluoroethylene may be mixed into the substance of or with the micro particles, and furthermore may thereafter be coated with a layer of a hyaluronate or hyaluronic acid. Specifically, certain modifiers such as polytetrafluoroethylene may be admixed with, for example, a poly di-substituted siloxane particle material prior to cure to impart an average surface modification to the cured particle. A material such as hyaluronic acid may be attached to the micro particle surface either through physical or chemical bonding. Surface modifiers also can be used to typically assist in detoxification and promote the desired tissue ingrowth encapsulation. Other bioactive substances that can be included in the carrier or attached to the surface of the beads to promote encapsulation include fibronectin, transforming growth factor beta, and various other cytokines such as interleukin-1.

Once implanted, the body will form a thin scar tissue around each of the implants so as to provide initial encapsulation. Polyvinylpyrrolidone, hyaluronate or collagen or other biocompatible substances may be chemically or physically combined with the particle substance or its surface to enhance the acceptance of the implant by the host. While in most situations the particles are of random size and configuration, but within the constraints of size indicated, it is generally desirable that the particles be of generally uniform configuration whenever possible.

For example, for soft tissue, a soft elastomer such as silicone rubber is a desirable material for the textured particles. When a firm area is being treated, such as connective tissue or the like, polytetrafluoroethylene (Teflon) or polyethylene may be satisfactorily utilized. In those instances wherein the requirement is for hard substances, biocompatible materials such as certain calcium salts including hydroxyapatite or other such crystalline materials, biocompatible ceramics, biocompatible metals such as certain stainless steel particles, or glass may be utilized.

By way of further background, the average diameter of a capillary is approximately 16 microns, or roughly two times the diameter of a red cell. Therefore, since the size of the textured micro particles is in the area of at least approximately 30 microns, they will not be absorbed into the capillaries, but will on the other hand, remain generally captive and fixed in place. Smaller particles, in the submicron range, have been implicated in causing inflammation and may be ingested by host cells. Thus, particles in the range of between about 30 and 3000 microns are employed.

The fibroblast cell is the scar-forming cell of the human body, and these cells range in size from between about 20 microns up to about 100 microns, and because of contact guidance, it will form a scar tissue or collagen-based coating around an inert foreign body. Furthermore, such scar tissue will conform to the irregularities in the surface of the foreign body, particularly if they are of sufficient size to accommodate tissue ingrowth. Our previous studies (American Society of Artificial Internal Organs; U. S. Pat. Nos. 3,638,649; 3,657,744; 4,239,492; and 4,240,794) have shown that foreign substances can be substantially firmly anchored in a predetermined location in the body. Because of the inherent ability of fibroblasts to form scar tissue in and around irregularities of the surface, such anchoring occurs in many locations, including locations within the blood stream.

Therefore, it is a primary object of the present invention to provide an improved method and apparatus for use in reconstructive surgical procedures, with the method employing textured micro particles which may be injected along with an appropriate physiologic vehicle into a predetermined locus within the body.

It is yet a further object of the present invention to provide an improved method and apparatus for use in reconstructive surgical procedures wherein textured micro particles having an outside diameter of between about 30 and 3000 microns may be employed along with an appropriately selected physiologic vehicle for implantation or injection into a predetermined locus.

It is yet a further object of the present invention to provide an improved method and apparatus for use in reconstructive surgical procedures wherein textured micro particles having an outside diameter of between about 30 and 3000 microns may be injected into a predetermined locus of the body for the purpose of filling of defects in reconstructive surgery, with a syringe device having an inwardly tapered out-flow tract being desirable for use with particles having a size within the upper range.

Other and further objects of the present invention will become apparent to those skilled in the art upon a study of the following specification, appended claims, and accompanying drawings.

IN THE DRAWINGS

FIG. 1 is a perspective view of a textured micro particle useful in accordance with the present invention, and illustrating surface irregularities typically present in the particle;

FIG. 2 is a vertical sectional view taken along the line and in the direction of the arrows 2—2 of FIG. 1;

FIG. 3 is a schematic illustration of a fragmentary portion of human skin organ, and illustrating a hypodermic needle of appropriate size being utilized to introduce materials in accordance with the present invention into the subcutaneous zone beneath a depressed scar;

FIG. 4 is a view similar to FIG. 3, and illustrating the same location following subcutaneous injection of the textured micro particles in accordance with the present invention;

DESCRIPTION OF THE PREFERRED EMBODIMENT

Figure 5:
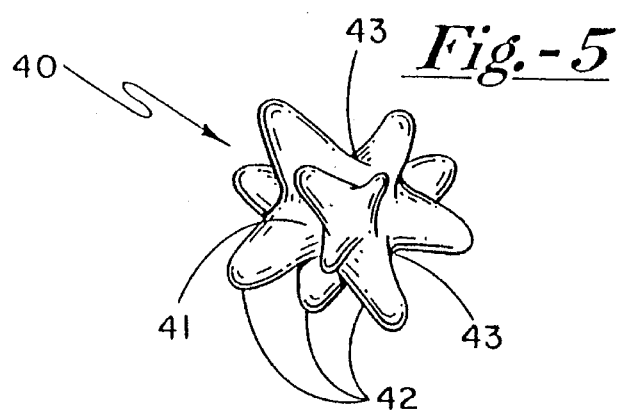
FIG. 5 is a perspective view of a modified form of useful particle wherein the surface irregularities project outwardly from a body member in pillar form, with the central body portion being in the form of a spheroid.

With attention being directed to FIG. 1 of the drawings, it will be observed that a micro-implant particle generally designated 10 comprises an inner-core having randomly distributed throughout its surface, various surface irregularities indentations interstices, cavities, openings or pores 11—11. These pores referred to collectively as pores are spaced apart by connective pillar members 12. As indicated above, the pores preferably have a minimum indentation depth or open dimension of about 10 Angstroms, along with a maximum dimension of about 500 microns. The interconnective or pillar zones 12—12 which separate or otherwise define solid material between pores 11—11 have a dimension or breadth sufficient so that the majority or greater portion of the surface is defined by indentations, pores.

With continued attention being directed to FIGS. 1 and 2 of the drawings, connective elements 12 are available on the surface of the micro-implant particles and provide for mechanical stability of the individual particle. This arrangement is illustrated in particular in FIG. 2.

In accordance with the present invention, it has further been found that inert foreign tissue augmentation particulate matter having a mean diameter less than about 30 microns will generally become subject to significant migratory loss from the site of injection regardless of surface configuration absent extraordinary protection. The textured nature of the surface of the microspheres of the invention, however, imparts to them an apparent size equivalency which, in the case of at least the relatively smaller sized particles (particularly in the range of 30–60 and up to 80 microns), makes them behave, once injected, as much larger smoother particles might behave with respect to host implant or prosthesis migration tendencies and benign assimilation in scar tissue. Particulate matter of the class of the present invention which is of a preferred size ranging from about 30 microns to about 3000 microns and having a textured surface in which the surface irregularities vary in size over a range of about 10 Angstroms to 500 microns.

The irregularities, pores and interstices are designed to have widths ranging from those having a diameter or opening size which will just accommodate the infiltration of a typical connective tissue fibril or protein molecule at the lower end to those large enough to accommodate ingrowth of much larger cross-linked protein, possibly collagen protein, fibrillar structures or actual fibroblasts at the high end. In this regard, it is well known that the collagen fiber is composed of fibrils and filaments. The basic poly-peptide chain is arranged into micro-filaments of tropocollagen having a diameter of approximately 20 Angstroms. It has been found that surface irregularities as small as 10 Angstroms will interdigitate with the filaments on the surface of the fibers and serve to resist host-prosthesis interface motion.

Further, with respect to particle size, it will be appreciated that particle size, particularly of those species contained in preparations utilized in prior injectable compositions, tends to vary over a range within any group of particles so that there will be a percentage of the group larger and a percentage of the group smaller than at target size in any such composition. In addition, the shape and size of the pores associated with a given group of particles will also describe a range. It will further be appreciated that one must take into account the normal variation in patient-to-patient acceptance and reaction to tissue augmentation injection of micro particles. With this in mind, certain observations have been made regarding optimum particle size, particularly with regard to the severe problems of unwanted migration and formation of granulomatous reactions.

Observations in a variety of clinical situations indicate that particles less than about 60 microns in diameter can be engulfed by macrophages and transported to regional lymph nodes. Submicron-sized particles may be the most easily transported and may remain intracellular indefinitely. However, larger particles, particles that approach the size of a macrophage, i.e., from about 20 to about 60 microns, may cause the death of a cell when engulfed. This begins a progression in which the dead cell releases its intercellular enzymes (cytokines), and those attract other phagocytes which, again, encounter and engulf the particle with the debris of the first encounter. In this manner, a vicious cycle continues on a larger scale as a chronic inflammatory response. Of course, such a response is highly undesirable.

Particles greater than about 60 microns, however, have not been observed within a cell or within lymph nodes; and, certainly, particles greater than 80 microns appear safe from initiating such foreign body reactions. Further, as in the example below, particles of an average diameter of 100 to 600 microns with textured surfaces having an average pore size from about 10 microns to about 200 microns have been observed to work quite well. Theoretically, there is no upper limit to the size of the textured particles, and this is borne out by the success of sintered-surface hip implants, textured breast implants and others. However, the useful upper limit of micro implant dimensions is probably somewhere in the vicinity of 1 to 3 mm in defects just beneath the skin surface because particles of a size greater than this may be perceived as surface irregularities when palpitated. Large textured implants have also been employed in breast reconstruction, for example.

It will be appreciated that textured spheroids of the class contemplated for use in the present invention may be molded, for example, by any gravity-free technique wherein the spheroids are formed with centrifugal force equal to that of gravity in cases where the spheroids are formed of rather malleable synthetic material. Spheroids can be fabricated from a variety of inert substances such as polytetrafluoroethylene, poly(methyl-methacrylate), poly substituted siloxanes (silicones) and a variety of other synthetic polymeric materials, ceramics and others and different fabrication processes may be applicable to each material for the augmentation of soft tissue. Of course, fabrication of the spheroids from a malleable polymer material such as a silicone rubber is preferred as it will more closely imitate the texture of the natural tissue it replaces. With respect to malleable polymers such as silicone rubber, the following fabrication techniques are exemplary of those that will readily enable manufacture by those skilled in the art. It will be appreciated that a technique that might be preferred for one material may not work equally well for all.

In one process, a malleable stock of unvulcanized polydimethylsiloxane is rolled into spheroids of approximately 100 microns or other desired size diameter. The surface is then textured by impacting each spheroid with an appropriate force. The textured spheroids are then vulcanized and mixed with the appropriate vehicle for injection.

In another successful method, generally preferred for forming beads of silicone rubbers, poly(di-substituted siloxane) silicone rubber of the type desired, normally poly(dimethyl siloxane) may be dispersed in an appropriate volatile solvent and then partially cured by droplets being forced through a specific distance of air from an orifice having a specific diameter. This is a very familiar process technique generally known with respect to the operation of a shot tower in making lead shot. The size of the beads or spheroids is easily regulated by varying the viscosity of the mixture and/or the orifice of origin. As the particle travels a known distance through air, it is partially cured as the volatile vehicle evaporates. The specifically formed spheroid or bead is then separated by a suitable fluid medium. The spheroids may then be pressed against an appropriate surface or impacted by an appropriate force to impart the desired texture, the surface having an appropriate mold release. Partially cured spheroids are then vulcanized by heat irradiation. The particles are then sized and graded by physical means. Spheroids are then mixed with the appropriate vehicle in appropriate ratios, placed in containers and finally sterilized within the container.

Texture can be imparted to the beads or spheroids in a number of ways. In addition to the molding method, other techniques include ion-beam microtexturing which makes it possible to produce controlled microtextured surfaces, chemical and plasma etching and impacting the beads with solid particles. Of course, it is contemplated that other methods could also occur to those skilled in the art.

If desired, surface modifiers, as explained above, can be incorporated in the material prior to formation of the spheroids or beads or may be thereafter be added as a coating on the deformed surfaces. In this manner, certain materials such as hyaluronic acid, for example, may be attached to the micro particle surface either through physical or chemical bonding in a well-known manner after formation and texturing.

EXAMPLE I

Amounts of particles with average diameters of 100, 150 and 600 micrometers were fabricated with a textured surface from fully polymerized and vulcanized poly(dimethylsiloxane). The polymer was mixed to form a biocompatible solution with an organic polymer hydrogel. The hydrogel was a polyvinylpyrrolidone gel having an average molecular weight of approximately 13,700 and one of a family of such material known as Plasdones. These materials in the molecular weight range of interest are freely transported through tissue fluids and excreted unchanged by the kidneys. The mixture utilized was approximately 38% by weight of the polymer and 62% of the gel material. The polymer/gel mixture was diluted with deionized water, mixed until the inert particles were evenly dispersed and then placed in 1-cc cylinders with small pistons placed in the proximal ends. The distal end of each cylinder would be attached to a 1-cc syringe with a Luer lock on the end and a piston member could be inserted in the proximal barrel. A highly leveraged injection ratchet mechanism was utilized to accept the syringe cartridges and deliver precise amounts of the gel mixture through a cannula into the subcutaneous plane of the ear tissue of 20 large, adult white rabbits. Controls using commercially available collagen derivatives were injected in the subcutaneous plane in adjacent sites in the rabbits' ears using small gauge needles provided by the manufacturers of the collagen derivatives.

With respect to the injected collagen control sites, subsequent histologic sections indicated that after three weeks, no residual collagen could be found at the site of the injection. In dramatic contrast, the histologic sections of the micro particles evidenced a dramatic transition in which the gel phase of the material was replaced by a fibrin and protocollagen matrix surrounding each of the micro particles. In three days, the fibrin matrix was complete, with all the gel having been removed by the host. Connective-tissue cells had developed and had begun to replace the matrix with host collagen fibrils. By the sixth week, this fibrosis was complete, and each individual textured particle appeared to be encased in its own individual inner connected covering of fibrous tissue. The thickness of the implanted area and the degree of fibrosis as measured by transillumination, micrometer and light and electron beam microscopy remained constant for more than a year.

Subsequent histologic examination of the regional lymph nodes at the base of the rabbit ears revealed no migration of particles. Cross-sections of the ear below the injected area showed no particles. Through transillumination, the size and density of the areas of injection were easily and atraumatically monitored for each rabbit. No textured micro implants were found at the base of the ears or in the regional lymph nodes of any of the rabbits under study.

The dimensions of the subcutaneous deposits of textured micro implants remained approximately the same throughout the period of study, as was evidenced by transillumination photographic record and micrometer measurement. Opacity was noted to decrease over the last few weeks as the transillumination became brighter but then appeared to stabilize between the end of the first and the sixth months.

The results obtained with the experimental particles of Example 1 illustrate the dramatic contrast between this material and the injection of collagen-containing materials. Although the collagen-containing materials created immediate soft tissue augmentation, these substances—which are only about 3.5 to 6.5% solid collagen material—soon became invaded by host capillaries and were absorbed. No absorption or migration of the 100, 150 or 600 micron silicone rubber particles was observed, even after 382 days.

In other experiments, particles having an average diameter of 80 microns and incorporating tracer material in the form of gamma radiation-emitting material were injected into the ears of other rabbits. These particles showed no migration from the injection site during a subsequent six-month monitoring period.

While prior work by the inventors and others have shown that surface irregularities preferably are in the 20 to 200 micron range in order to achieve adequate contact guidance of the fibroblasts so as to create or develop a scar tissue pattern that is a mirror image of the substrate surface, it is also appreciated that the particle size in relation to the relative size of the surface irregularities is a factor to be considered. In this connection, if the openings, pores are too shallow in their depth dimension, or in the event their diameter is not sufficiently great, the fibroblasts will tend to bridge across the defect so as to provide a substantially smooth surface. In the preferred embodiment of the present invention, the particles indicated or selected for a specific procedure to assist in correcting a given defect are previously loaded into a hypodermic syringe with a needle having an adequately sized interior bore so that upon injection of the needle into the area of the depression being corrected, the particles together with the appropriate physiologic vehicle enables the spheroids to be injected directly into the area of the depression. Appropriate vehicles, as previously indicated, include physiologic saline or polysaccharide lubricants, each of these enabling the spheroids to be injected as set forth.

With attention being directed to FIG. 3 of the drawings, it will be noted that surface tissue as shown at 20 includes a depression area 21, with the depression area extending into the subcutaneous tissue as at 22. For utilization of the concept of the present invention, the needle 23 is shown as it is injected into tissue. Particles 30, of the type illustrated in FIGS. 1 and 2, along with vehicle 31 are injected into the predetermined site, with the result being filling of the depression area, particularly as illustrated in FIG. 4. Upon withdrawal of the needle 23, the injected material is left in situ at the selected site. The supply of particles 30 retained and carried within vehicle 31 may be conveniently retained in syringe body zone 23A for passage through hollow needle 23. Syringes of this type are, of course, commercially available, and suitable for particles in the low to mid-size range, while larger particles within the size range may require an inwardly tapered out-flow tract. For certain applications, it has been found desirable to utilize a syringe-needle combination which tapers continuously, thereby providing an elongated syringe-needle combination with a inwardly tapered out-flow tract.

Generally, upon completion of the inflammatory phase of wound healing, or after approximately one week, formation of scar tissue commences with this becoming complete after about three weeks. Following completion of the deposition and formation of scar tissue, a remodeling phase or operation may be undertaken. In view of the specific irregularities and indentations of the surfaces of the individual particles, contact guidance will normally allow for the resulting scar tissue to firmly anchor and attach the implanted particles 30 wherever deposited. As borne out by the example, although various biological substances have been used for similar purposes, such as collagen and fibril, these other previously utilized substances are normally broken down by the body over a period of time and digested autogenously. It is anticipated that the micro particles fabricated of silicone rubber, polytetrafluoroethylene (Teflon), ceramic or other appropriate inert substances will mimic the durometer hardness of the host tissue being filled, with the softer materials, such as silicone rubber being utilized for normal subcutaneous fat tissue, and with ceramic materials being utilized for bone tissue. Polytetrafluoroethylene (Teflon) is deemed suitable for cartilage, and silicone elastomer with variations in firmness for subcutaneous fat in various regions of the body. In the event the procedure involves an over-correction, the use of lipoplasty techniques of suction lipectomy with a cannula of appropriate diameter will allow for fine tuning, even after several months or years. Removal of an appropriate quantity of filler material may be accomplished in that fashion.

Figure 6:
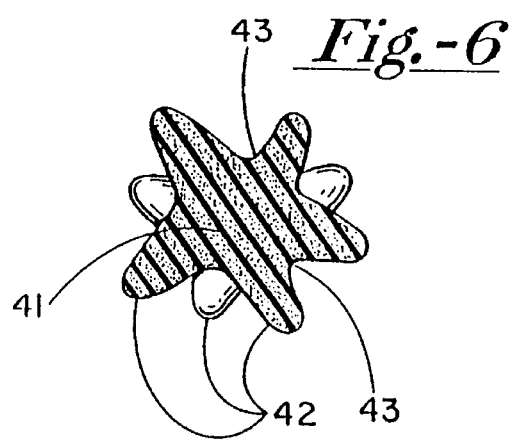
FIG. 6 is a cross-sectional view of the device of FIG. 5.

Specific attention is now directed to the modification of particle configuration illustrated in FIGS. 5 and 6. Specifically, the textured micro particle generally designated 40 comprises a central body portion 41 of generally spheroidal form, together with a number of outwardly projecting pillar members 42—42 thereon. Inter-pillar indentations of generally arcuate form are shown at 43—43. Textured micro particles of the type illustrated in FIGS. 5 and 6 may also be found useful in connection with the various aspects of the present invention. In actual use, these micro particles will be combined with an appropriate vehicle, of the type previously referred to, such as physiologic saline, PVP or polysaccharide lubricant, so as to enable these textured micro particles to be injected into the body. Also, textured micro particles of the type illustrated in FIGS. 5 and 6 may be formed of the same material as indicated in connection with the embodiment of FIGS. 1–4, such as for example, silicone rubber, polytetrafluoroethylene (Teflon), biocompatible solids such as, for example, hydroxyapatite or other biocompatible solids of the type listed hereinabove.

Radiopaque substances may be utilized, such as, for example, barium compounds to make the particles more visible. Radioactive materials may also be incorporated for certain applications. In most instances, however, utilization of such radiographic tagging will not be required.

It will be appreciated that the specific examples provided herein are given for purposes of illustration only, and are not to be construed as a limitation upon the scope of the present invention, and that those skilled in the art may depart from the specific examples without actually departing from the spirit and scope of the present invention.

What is claimed is:

1. An injectable particulate implantation system for long-term augmentation of soft tissue, comprising in combination:

(a) an amount of generally soft, malleable, elastic, biologically compatible non-resorbin prosthetic particles dispersed in a non-retentive compatible physiological vehicle, said particles being further characterized by a rough surface texture having a plurality of surface irregularities generally randomly formed therein;

(b) said implantation system incorporating a combination of average particle size and average particle texture sufficient to cooperate in an autogenous manner to substantially prevent loss of said particles from an augmentation site, said particles remaining in situ to form part of a permanent implant.

2. The injectable implantation system of claim 1 being particularly characterized in that the range of average particle size is between 100 microns to 600 microns.

3. An injectable particulate implantation system for long-term augmentation of soft tissue, comprising in combination:

(a) biologically compatible particles of a relatively soft, resilient, non-resorbing material dispersed in a non-retentive compatible physiological vehicle, the particles being further characterized by a rough surface having a plurality of surfaces irregularities randomly formed therein and further comprising openings or pores;

(b) the particles having an average particle size generally between 30 and 3000 microns with a dimension of the openings formed by the pores within the particles being generally in a range between 10 angstroms and 500 microns;

(c) wherein the implantation system average particle size and average roughness of texture are sufficient in combination to, in an autogenous manner, substantially preclude migration of the particles from an augmentation site, such that the particles remain in situ to form part of a permanent implant.

4. The injectable implantation system of claim 3 wherein the particles further comprise an amount of at least one surface modifier to accomplish at least one of assisting in detoxification and promoting tissue ingrowth.

5. The injectable implantation system of claim 4 wherein the at least one surface modifier is incorporated into the micro particle prior to particle formation.

6. The injectable implantation system of claim 4 wherein the at least one surface modifier is selected from the group consisting of polyvinyl pyrrolidone, collagen and an hyaluronate.

7. The injectable implantation system of claim 6 wherein the surface modifier is dispersed in the physiological vehicle.

8. The injectable implantation system of claim 7 wherein the surface modifier is biologically active.

9. The injectable implantation system of claim 4 wherein the surface modifier is biologically active.

10. The injectable implantation system of claim 4 wherein the modifier is selected from the group consisting of fibronectin and cytokines.

11. The injectable implantation system of claim 3 being particularly characterized in that the compatible physiological vehicle is a bodily compatible fluid selected from the group consisting of hydrogels, glucose, starch, silicone fluid, lipid and a hyaluronate.

12. The injectable implantation system of claim 3 being particularly characterized in that the biologically inert particles are formed of bodily compatible solids selected from the group consisting of silicone rubbers, polytetrafluoroethylene, polyethylene, and other biologically inert polymer materials.

13. The injectable implantation system of claim 12 being particularly characterized in that the average particle size is at least 60 microns.

14. The injectable implantation system of claim 13 further characterized by micro particles having a textured surface of pores of an average size between about 10 microns and about 200 microns.

15. The injectable implantation system of claim 12 being particularly characterized in that the range of average particle size is between 100 microns to 600 microns.

16. The injectable implantation system of claim 3 being particularly characterized in that the average particle size is at least 60 microns.

17. The injectable implantation system of claim 16 being particularly characterized in that the biologically inert micro particles are of a generally uniform configuration.

18. The injectable implantation system of claim 3 being particularly characterized in that the range of average particle size is between 100 microns to 600 microns.

19. A non-migratory injectable particulate implantation system for long-term augmentation of soft tissue, comprising in combination:

(a) generally soft, resilient biologically inert, micro particles of a material of a material not resorbed by the body dispersed in a non-retentive compatible physiological vehicle, the micro particles being further characterized by a surface texture having a plurality of surface irregularities generally randomly formed therein;

(b) said implantation system having, in combination, an average particle size range and average particle texture such that migration from an injection site is substantially precluded in an autogenous manner and individual particle non-chronic inflammatory scar tissue encapsulation occurs, said particles thereby remaining in situ to form part of said implantation system.

20. An injectable particulate implantation system for long-term augmentation of soft tissue, comprising in combination:

(a) generally soft, resilient biologically inert nonresorbing implant particles having a generally rough surface dispersed in a non-retentive compatible physiological vehicle, the micro particles being of a generally uniform configuration and being further characterized by a surface texture having a plurality of surface irregularities separated by connective members generally randomly formed therein;

(b) the textured particles being formed of materials selected from the group consisting of silicone rubbers, polytetrafluoroethylene, polyethylene, and other biologically inert polymer materials, and having an average particle size generally between 60 and 3000 microns with dimensions of surface irregularities within the particles being generally in a range between 10 angstroms and 500 microns; and (c) said implantation system incorporating an average particle size and average texture roughness to, in combination in an autogenous manner, substantially preclude migration of said particles from an injection site and achieve adequate guidance of fibroblasts such that a scar tissue pattern is developed that assumes a configuration that is generally in accordance with adjacent particle surfaces, said particles thereby remaining in situ to form a permanent part of said implantation system.

* * * * *

UNITED STATES PATENT AND TRADEMARK OFFICE
CERTIFICATE OF CORRECTION

PATENT NO.   : 5,571,182
DATED        : November 5, 1996
INVENTOR(S)  : Robert A. Ersek et al It is certified that error appears in the above-indentified patent and that said Letters Patent is hereby corrected as shown below:

In column 10, claim 1(a), line 12, please delete "non-resorbin" and insert -- non-resorbing --.

In column 11, claim 19(a), line 35, please delete the first "of a material".

Signed and Sealed this

Fourth Day of March, 1997

Attest:

BRUCE LEHMAN

*Attesting Officer*   *Commissioner of Patents and Trademarks*